US007125819B2

(12) United States Patent
Van Der Linden et al.

(10) Patent No.: US 7,125,819 B2
(45) Date of Patent: Oct. 24, 2006

(54) CATALYST PREPARATION

(75) Inventors: Johannes Petrus Van Der Linden, Amsterdam (NL); Eduardus Petrus Simon Schouten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 5 days.

(21) Appl. No.: 10/720,905

(22) Filed: Nov. 24, 2003

(65) Prior Publication Data

US 2004/0116723 A1    Jun. 17, 2004

(30) Foreign Application Priority Data

Dec. 2, 2002  (EP)  .................. 02258294
Dec. 2, 2002  (EP)  .................. 02258296

(51) Int. Cl.
  *B01J 31/00*  (2006.01)
(52) U.S. Cl. .................................... 502/102
(58) Field of Classification Search ............... 502/105, 502/107
See application file for complete search history.

(56) References Cited

U.S. PATENT DOCUMENTS

| 3,829,392 A | 8/1974 | Wulff .................. 252/430 |
| 3,923,843 A | 12/1975 | Wulff .................. 260/348.5 |
| 6,383,966 B1 | 5/2002 | Han et al. |

FOREIGN PATENT DOCUMENTS

| EP | 345856 | 8/1992 |
| EP | 345856 A | 8/1992 |
| EP | 525503 | 2/1993 |
| EP | 734764 | 10/1996 |
| WO | 95/07305 | 3/1995 |
| WO | 02/48126 | 6/2002 |

*Primary Examiner*—Taofiq Solola

(57) ABSTRACT

The invention relates to a process for the preparation of an epoxidation catalyst, which process involves impregnating a silicon containing carrier with a gas stream consisting of titanium halide. The invention also relates to a process for the preparation of alkylene oxide using such catalyst.

34 Claims, No Drawings

CATALYST PREPARATION

FIELD OF THE INVENTION

The present invention relates to the preparation of an epoxidation catalyst and to the process of preparing an alkylene oxide by using such catalyst.

BACKGROUND OF THE INVENTION

An epoxidation catalyst is understood to be a catalyst which catalyzes the manufacture of an epoxy group containing compound. One process comprises contacting a hydroperoxide and an alkene with a heterogeneous epoxidation catalyst and withdrawing a product stream comprising alkylene oxide and an alcohol.

Catalysts for the manufacture of an epoxy group containing compound are known. EP-A-345856 describes the preparation of such catalyst comprising titanium in chemical combination with a solid silica and/or inorganic silicate. The preparation comprises (a) impregnating a silicon compound with a stream of gaseous titanium tetrachloride preferably comprising an inert gas, (b) calcining the obtained reaction product of step (a), and (c) hydrolyzing the product of step (b). The stream of inert gas also has the function of a carrier for the gaseous titanium tetrachloride. For such use, the gas is to be present in a relatively large amount.

There is a continuous interest in improving the selectivity of epoxidation processes in general, and more specifically of processes for the preparation of alkylene oxides.

SUMMARY OF THE INVENTION

The present invention provides a process for the preparation of an epoxidation catalyst, which process comprises impregnating a silicon containing carrier with a gas stream consisting of titanium halide.

DETAILED DESCRIPTION OF THE INVENTION

The catalyst of the present invention may be obtained by impregnating a silicon containing carrier. In principle, any silicon containing carrier may be suitable for use in the preparation process according to the present invention. Examples of silicon containing carriers comprise zeolites. Preferably, the silicon containing carrier is a silica carrier.

Silica carriers will substantially consist of silicon dioxide. However, limited amounts of further compounds such as contaminants may be present as well.

It is known that contaminants can influence the performance of the final catalyst. The silica carrier for use in the present invention preferably contains at most 1200 ppm of sodium, more specifically at most 1000 ppm of sodium. Further, the silica carrier preferably comprises at most 500 ppm of aluminum, at most 500 ppm of calcium, at most 200 ppm of potassium, at most 100 ppm of magnesium and at most 100 ppm of iron. The amounts are based on amount of carrier.

The silica carrier preferably is a silica gel. The silica gel carrier for use in the present invention may in principle be any carrier derived from a silicon containing gel. In general, silica gels are a solid, amorphous form of hydrous silicon dioxide distinguished from other hydrous silicon dioxides by their microporosity and hydroxylated surface. Silica gels usually contain three-dimensional networks of aggregated silica particles of colloidal dimensions. They are typically prepared by acidifying an aqueous sodium silicate solution to a pH of less than 11 by combining it with a strong mineral acid. The acidification causes the formation of monosilicilic acid ($Si(OH)_4$), which polymerizes into particles with internal siloxane linkages and external silanol groups. At a certain pH the polymer particles aggregate, thereby forming chains and ultimately gel networks. Silicate concentration, temperature, pH and the addition of coagulants affect gelling time and final gel characteristics such as density, strength, hardness, surface area and pore volume. The resulting hydrogel is typically washed free of electrolytes, dried and activated. A suitable silica gel carrier would be silica support V432 and DAVICAT® P-732, which are commercially available from Grace Davison.

Silica gel carriers for use in the present invention preferably have a weight average particle size of at most 2 mm. Particle sizes which were found to be especially suitable were weight average particle sizes of from 0.2 mm to 1.8 mm, more specifically from 0.4 mm to 1.6 mm, most specifically from 0.6 mm to 1.4 mm.

The silicon containing carrier preferably has a low water content when contacted with the titanium halide. A low water content can be achieved in any way known to someone skilled in the art. A preferred way comprises drying the silicon containing carrier before impregnating the silicon containing carrier with the gas stream consisting of titanium halide. A suitable drying method comprises subjecting the silicon containing carrier to a temperature of from 200° C. to 700° C. The preferred drying conditions comprise drying the carrier at a temperature of from more than 200° C. to 300° C. The drying is preferably carried out for a period of time ranging from 1 hour to 8 hours, preferably in the presence of an inert gas such as nitrogen. The preferred method has been described in more detail in co-pending patent application claiming priority of European application 02258294.4, which is hereby incorporated by reference.

A further improvement was observed if the silicon containing carrier was subjected to a pretreatment comprising calcining the silicon containing carrier and subsequently hydrolyzing the carrier obtained. Hydrolysis comprises treating the carrier with water or steam. Preferably, the hydrolysis is carried out with steam. Alternatively, the hydrolysis treatment may comprise a washing treatment using an aqueous solution of a mineral acid, an aqueous solution of an ammonium salt or a combination thereof. Any water which might still be present after the hydrolysis is preferably removed before treating the carrier further. Water is preferably removed by drying. Preferably, the calcination is carried out at a relatively high temperature. A preferred calcination treatment comprises (a) calcining a silica gel carrier at a temperature of at least 400° C., (b) hydrolyzing the calcined silica gel carrier, (c) impregnating the hydrolysed carrier obtained in step (b) with a titanium-containing impregnating agent, and (d) calcining the impregnated carrier. Preferably, the calcination of step (a) is carried out at a temperature of from 450° C. to 800° C., more preferably of from 500° C. to 700° C.

The silica gel carrier for use in the present invention preferably has a surface area of at most 1000 m²/gram, more preferably at most 800 m²/gram, most preferably at most 500 m²/gram.

Titanium halides which may be used in the process according to the present invention comprise tri- and tetra-substituted titanium complexes which have from 1 to 4 halide substituents with the remainder of the substituents, if any, being alkoxide or amino groups. The titanium halide can be either a single titanium halide compound or can be a mixture of titanium halide compounds. Preferably, the titanium halide comprises at least 50% wt of titanium tetrachloride, more specifically at least 70% wt of titanium tetrachloride. Most preferably, the gas stream consists of titanium tetrachloride.

The present invention comprises impregnating the carrier with gas consisting of titanium halide. Surprisingly, it was found that a catalyst having higher selectivity for the desired alkylene oxide could be obtained if the silicon containing carrier was impregnated with gas consisting of titanium halide. The preparation according to the present invention is carried out in the absence of a carrier gas. Without wishing to be bound to any theory, it is thought that the carrier gas interferes with the impregnation. However, limited amounts of further gaseous compounds may be present during the contact between the silicon containing carrier and the gaseous titanium halide. The gas in contact with the carrier during impregnation preferably comprises at least 80% wt of titanium halide, more specifically at least 90% wt, most specifically at least 95% wt.

Gaseous titanium halide can be prepared in any way known to someone skilled in the art. A simple and easy way comprises heating a vessel containing titanium halide to such temperature that the gaseous titanium halide is obtained.

Generally, the impregnated carrier will be calcined and subsequently hydrolyzed before being used as a catalyst. It is believed that calcination removes hydrogen halide, more specifically hydrogen chloride which is formed upon reaction of titanium halide and silicon compounds present on the surface of the silicon containing carrier.

The optional calcination of the impregnated carrier generally comprises subjecting the impregnated carrier to a temperature of at least 500° C., more specifically at least 600° C. Preferably, the calcination is carried out at a temperature of at least 650° C. From a practical point of view, it is preferred that the calcination temperature applied is at most 1000° C.

Hydrolysis of the impregnated and calcined carrier can remove titanium-halide bonds. The hydrolysis of the impregnated carrier will generally be somewhat more severe than the optional hydrolysis of the carrier before impregnation. Accordingly, this hydrolysis of the impregnated carrier is suitably carried out with steam at a temperature in the range of from 150° C. to 400° C.

Preferably, the hydrolyzed impregnated carrier is subsequently silylated, for instance, by contacting the hydrolyzed impregnated carrier with a silylating agent, preferably at a temperature of between 100° C. and 425° C. Suitable silylating agents include organosilanes such as tetra-substituted silanes with $C_1$–$C_3$ hydrocarbyl substituents. A very suitable silylating agent is hexamethyldisilazane. Examples of specific suitable silylating methods and silylating agents are, for instance, described in U.S. Pat. No. 3,829,392 and U.S. Pat. No. 3,923,843 which are referred to in U.S. Pat. No. 6,011,162, and in EP-A-734764, all of which are hereby incorporated by reference.

The amount of titanium (as metallic titanium) will normally be in the range of from 0.1% to 10% by weight, suitably of from 1% to 5% by weight, based on total weight of the catalyst. Preferably, titanium or a titanium compound, such as a salt or an oxide, is the only metal and/or metal compound present.

As mentioned above, alkylene oxides, such as propylene oxide, may be produced by epoxidation of the corresponding olefin using a hydroperoxide such as hydrogen peroxide or an organic hydroperoxide as the source of oxygen. The hydroperoxide may be hydrogen peroxide or any organic hydroperoxide such as tert-butyl hydroperoxide, cumene hydroperoxide and ethylbenzene hydroperoxide. The alkene may be propene which results in propylene oxide as the alkylene oxide. The catalyst prepared according to the present invention has been found to give especially good results in such process. Therefore, the present invention further relates to a process for the preparation of alkylene oxide which process comprises contacting a hydroperoxide and alkene with a heterogeneous epoxidation catalyst and withdrawing a product stream comprising alkylene oxide and an alcohol and/or water, in which process the catalyst has been prepared according to the present invention.

A specific organic hydroperoxide is ethylbenzene hydroperoxide, in which case the alcohol obtained is 1-phenylethanol. The 1-phenylethanol may be further converted by dehydration to obtain styrene.

Another method for producing propylene oxide is the co-production of propylene oxide and methyl tert-butyl ether (MTBE) starting from isobutane and propene. This process involves similar reaction steps as the styrene/propylene oxide production process described in the previous paragraph. In the epoxidation step, tert-butyl hydroperoxide is reacted with propene forming propylene oxide and tert-butanol. Tert-butanol is subsequently etherified into MTBE.

A further method comprises the manufacture of propylene oxide from cumene. In this process, cumene is reacted with oxygen or air to form cumene hydroperoxide. Cumene hydroperoxide thus obtained is reacted with propene in the presence of an epoxidation catalyst to yield propylene oxide and 2-phenyl propanol. The latter can be converted into cumene via a heterogeneous catalyst and hydrogen. Suitable processes are described for example in WO 02/48126, which is hereby incorporated by reference.

The conditions for the epoxidation reaction according to the present invention are those conventionally applied. For propene epoxidation reactions using ethylbenzene hydroperoxide, typical reaction conditions include temperatures of 50° C. to 140° C., suitably 75° C. to 125° C., and pressures up to 80 bar with the reaction medium being in the liquid phase.

The invention is further illustrated by the following Examples.

EXAMPLES

The silica gel carrier used in the examples had a surface area of 300 $m^2$/g and a weight average particle size of about 1 mm. Substantially all particles had a particle size between 0.6 and 1.4 mm.

75 grams of silica gel carrier was dried at 250° C. during 2 hours.

The dried silica gel carrier was contacted with a gas stream containing titanium tetrachloride. The gas stream was obtained by heating titanium tetrachloride to 200° C. using an electrical heating system. Different gas streams were obtained by adding different amounts of nitrogen. At the end of each experiment, each silica carrier had been in contact with the same amount of titanium tetrachloride.

The impregnated catalysts thus obtained were calcined at 600° C. during 7 hours. The calcined catalysts were subsequently contacted with steam at 325° C. for 6 hours. The steam flow consisted of 3 grams of water per hour and 8 Nl of nitrogen per hour. Finally, the catalysts were silylated at 185° C. during 2 hours by being contacted with 18 grams of hexamethyldisilazane per hour in a nitrogen flow of 1.4 Nl per hour.

The catalysts obtained were analyzed for the amount of titanium deposited on the carrier.

The selectivity of the catalysts was tested in a continuous epoxidation bench scale unit containing a number of vessels on automatic weight balances containing respectively the ethylbenzene hydroperoxide and propene feed streams, two high pressure pumps, a fixed bed reactor, a third pump for pumping a recycle stream over the reactor, means to maintain the reactor continuously at temperatures between 60° C. and 120° C., a stripper to remove light boiling components like propene, a cooler and a vessel for receiving the product.

The feeds were supplied to the reactor via the two high pressure pumps and mixed together before entering the reactor. The reactor was operated liquid full at 40 bara pressure and 90° C. A large recycle stream was maintained over the reactor to have isothermal operation of the reactor bed and to ensure that the catalyst to be re-activated is contacted with epoxidation reaction product. The feed was mixed with the recycle stream prior to introduction into the reactor.

The feed consisted of 40% wt of propene, 20% wt of ethylbenzene hydroperoxide and 40% wt of ethylbenzene.

The results obtained are given in Table 1. The selectivity is the molar ratio of propylene oxide formed to ethylbenzene hydroperoxide converted.

Example 2

Further catalysts were prepared in a way similar to the one described in Example 1. However, the impregnated catalysts were calcined for 6 hours (instead of 7 hours) while the steam flow during the subsequent hydrolysis contained 5 grams of water per hour (instead of 3 grams of water per hour). The results of these experiments are shown in Table 2.

TABLE 1

|  | Example 1 | Comparative Example 1 | Comparative Example 2 |
| --- | --- | --- | --- |
| Impregnating gas |  |  |  |
| % wt titanium tetrachloride | 100 | 75 | 60 |
| Catalyst |  |  |  |
| titanium (% wt) | 4.1 | 4.0 | 4.1 |
| sodium (% wt) | 0.07 | 0.07 | 0.07 |
| Selectivity to propylene oxide |  |  |  |
| 100–200 hours on stream | 90.9 | 89.7 | 90.1 |
| 200–300 hours on stream | 91.3 | 90.4 | 91.1 |

TABLE 2

|  | Example 2 | Comparative Example 3 | Comparative Example 4 |
| --- | --- | --- | --- |
| Impregnating gas |  |  |  |
| % wt titanium tetrachloride | 100 | 26 | 1 |
| Catalyst |  |  |  |
| titanium (% wt) | 3.8 | 4.1 | 4.1 |
| sodium (% wt) | 0.07 | 0.05 | 0.07 |

TABLE 2-continued

|  | Example 2 | Comparative Example 3 | Comparative Example 4 |
| --- | --- | --- | --- |
| Selectivity to propylene oxide |  |  |  |
| 100–200 hours on stream | 90.5 | 89.6 | 88.4 |
| 200–270 hours on stream | 90.5 | 89.3 | 88.3 |
| 270–340 hours on stream | 92.5 | 91.2 | 90.6 |
| 370–420 hours on stream | 92.5 | 91.4 | 90.8 |

What is claimed is:

1. A process for the preparation of an epoxidation catalyst, which process comprises impregnating a silicon containing carrier with a gas stream consisting of titanium halide wherein said silicon containing carrier is a silica gel that substantially consists of silicon dioxide and contains, at most: (a) 1200 ppm of sodium, (b) 500 ppm of aluminum, (c) 500 ppm of calcium, (d) 200 ppm of potassium, (e) 100 ppm of magnesium, and (f) 100 ppm of iron, based on amount of carrier.

2. The process of claim 1 wherein the gas stream consists of titanium tetrachloride.

3. The process of claim 1, further comprising drying the silicon containing carrier before impregnation.

4. The process of claim 3, further comprising calcining and subsequently hydrolyzing the impregnated carrier to produce a calcined and hydrolyzed carrier.

5. The process of claim 4, further comprising contacting the hydrolyzed carrier with a silylating agent.

6. The process of claim 1, wherein the gas stream consists of titanium tetrachloride.

7. The process of claim 1, wherein the silicon containing carrier comprises particles with a weight average particle size of at most 2 mm.

8. The process of claim 1, further comprising drying the silicon containing carrier before impregnation.

9. The process of claim 1, further comprising calcining and subsequently hydrolyzing the impregnated carrier to produce a calcined and hydrolyzed carrier.

10. The process of claim 9, further comprising contacting the hydrolyzed carrier with a silylating agent.

11. The process of claim 10 wherein the silylating agent comprises hexamethyldisilazane.

12. The process of claim 3 wherein said silicon containing carrier is dried by heating said carrier at a temperature of from 200° C. to 700° C. for a time ranging from 1 hour to 8 hours.

13. The process of claim 12 wherein said temperature is from 200° C. to 300° C.

14. The process of claim 1 wherein said silicon containing carrier has a weight average particle size of from 0.2 mm to 1.8 mm.

15. The process of claim 14 wherein said particle size is from 0.4 mm to 1.6 mm.

16. The process of claim 15 wherein said particle size is from 0.6mm to 1.4 mm.

17. The process of claim 1 wherein said silicon containing carrier is a silica gel that has a surface area of at most 1000 $m^2$/gram.

18. The process of claim 1 wherein said silicon containing carrier has a surface area of at most 800 $m^2$/gram.

19. The process of claim 1 wherein said silicon containing carrier has a surface area of at most 500 m²/gram.

20. The process of claim 1 wherein said silicon containing carrier has a low water content.

21. The process of claim 4 wherein said silicon containing carrier is a silica having a low water content and a weight average particle size of at most 2 mm.

22. The process of claim 21 wherein said silica gel has a weight average particle size of from 0.4 mm to 1.6 mm and a surface area of at most 800 m²/gram.

23. The process of claim 22 wherein said silica gel has a weight average particle size of from 0.6 mm to 1.4 mm and a surface area of at most 500 m²/gram.

24. The process of claim 22 wherein said silica gel has a weight average particle size of from 0.2 mm to 1.8 mm and a surface area of at most 1000 m²/gram.

25. The process of claim 21 wherein said titanium halide is titanium tetrahalide.

26. The process of claim 21 further comprising contacting the hydrolyzed carrier with a silylating agent.

27. The process of claim 26 wherein the silylating agent comprises hexamethyldisilazane.

28. A process for the preparation of an epoxidation catalyst, which process comprises impregnating a silicon containing carrier with a gas stream comprising at least 80% wt of titanium halide wherein said silicon containing carrier is a silica gel that substantially consists of silicon dioxide and contains, at most: (a) 1200 ppm of sodium, (b) 500 ppm of aluminum, (c) 500 ppm of calcium, (d) 200 ppm of potassium, (e) 100 ppm of magnesium, and (f) 100 ppm of iron, based on amount of carrier.

29. The process of claim 28, wherein the gas stream comprises at least 90% wt of titanium halide.

30. The process of claim 29, wherein the gas stream comprises at least 95% wt of titanium halide.

31. The process of claim 28, wherein said titanium halide is titanium tetrachloride.

32. The process of claim 31, further comprising calcining and subsequently hydrolyzing the impregnated carrier to produce a calcined and hydrolyzed carrier.

33. The process of claim 32, further comprising contacting the hydrolyzed carrier with a silating agent.

34. The process of claim 33, wherein the silating agent comprises hexamethyldisilazane.

* * * * *